United States Patent [19]

Duffett

[11] Patent Number: Plant 5,811

[45] Date of Patent: Nov. 25, 1986

[54] CHRYSANTHEMUM PLANT NAMED EN GARDE

[75] Inventor: William E. Duffett, Salinas, Calif.

[73] Assignee: Yoder Brothers, Inc., Barberton, Ohio

[21] Appl. No.: 644,270

[22] Filed: Aug. 27, 1984

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named En Garde characterized as to uniqueness by the combined characteristics of flat capitulum form, decorative capitulum type, red-purple ray floret color, diameter across face of capitulum ranging from 9 to 10 cm. at maturity, uniform eight week flowering response, medium plant height, semi-spreading branching pattern, and tolerance of both low winter 13° C. minimum and high summer 24° C. night to 38° C. day temperatures for bud initiation and flower development.

3 Drawing Figures

The present invention comprises a new and distinct cultivar of *Chrysanthemum morifolium,* Ramat., named En Garde.

En Garde is a product of a planned breeding program which had the objective of creating new Chrysanthemum cultivars for pinched, disbud pot mum programs having decorative capitulum type, purple floret color, eight week flowering response and the ability to produce commercially acceptable quality in year round programs. Such traits in combination were not present or required improvement in previously available commercial cultivars.

En Garde was originated from a cross made in a controlled breeding program in Salinas, Calif. in 1979. The female parent was identified as 75237002 and known as Tempo. Tempo is disclosed in U.S. Plant Pat. No. 4,505 and was originated by the present inventor. The male parent of En Garde was identified as 78826009, an unnamed lavender decorative seedling originated from a cross between an unnamed seedling and Circus, disclosed in U.S. Plant Pat. No. 4,188.

En Garde was discovered and selected as one flowering plant within the progeny of the stated cross by William E. Duffett on June 16, 1980 in a controlled environment in Salinas, Calif.

The first act of asexual reproduction of En Garde was accomplished when vegetative cuttings were taken from the initial selection in October, 1980 in a controlled environment in Salinas, Calif. by a technician working under formulations established and supervised by William E. Duffett.

Horticultural examination of selected units initiated July 15, 1981 has demonstrated that the combination of characteristics as herein disclosed for En Garde are firmly fixed and are retained through successive generations of asexual reproduction.

En Garde has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of En Garde which in combination distinguish this Chrysanthemum as a new and distinct cultivar.

1. Flat capitulum form.
2. Decorative capitulum type.
3. Red-purple ray floret color.
4. Diameter across face of capitulum ranging from 9 to 10 cm. at maturity.
5. Uniform eight week photoperiodic flowering response to short days.
6. Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6″ pots).
7. Semi-spreading branching pattern.
8. Tolerance of low winter 13° C. minimum temperatures.
9. Tolerance of high summer 24° C. night and 38° C. day temperatures.

The accompanying photographic drawings depict typical leaf and inflorescence characteristics of En Garde.

Sheet 1 is a color photograph of a plant of En Garde grown as a pinched, disbudded pot mum, with colors being as accurate as possible with renditions of this type.

Sheet 2 is a black and white photograph of three views of the inflorescence of En Garde.

Sheet 3 shows the upper and under surfaces of leaves of En Garde in three stages of growth (mature, intermediate, immature).

Of the many commercial cultivars known to the present inventor, the most similar in comparison to En Garde in Tempo, disclosed in U.S. Plant Pat. No. 4,505. Reference is made to attached Chart A which compares certain characteristics of En Garde to those same characteristics of Tempo. Traits similar in both cultivars are the capitulum type, form, color and branching pattern. En Garde has a shorter response time, a smaller capitulum diameter, a shorter plant height, and its tolerance of high and low temperatures results in a longer period of flowering value.

In the following description, color references are made to The Royal Horticultural Society Colour Chart.

The color values were determined between 11:00 A.M. and 11:15 A.M. on Mar. 6, 1984 under 380 foot-candle light intensity at Salinas, Calif.

Classification:

*Botanical.*—*Chrysanthemum morifolium,* Ramat., cv En Garde.

*Commercial.*—Decorative disbud pot mum.

I. INFLORESCENCE

A. Capitulum:

*Form.*—Flat.

*Type.*—Decorative.

*Diameter across face.*—9 to 10 cm.

B. Corolla or ray florets:

*Color (general tonality from a distance of three meters).*—Red-purple.

*Color (upper surface).*—78B-78C.

*Color (under surface).*—78D.

*Shape.*—Oblong. Rounded tip.

C. Corolla of disc florets:

*Color (mature).*—2B.

*Color (immature).*—154A.

D. Reproductive organs:

*Androecium.*—Present disc florets only; scant pollen.

*Gynoecium.*—Present both ray and disc florets.

II. PLANT

A. General appearance:

*Height.*—Medium.

*Branching pattern.*—Semi-spreading.

B. Foliage:

*Color (upper surface).*—147A.

*Color (under surface).*—147C.

*Shape.*—Narrow, shallow lobes. Blunt with minimum serration.

CHART A

COMPARISON OF EN GARDE AND TEMPO

| CULTIVAR | RAY FLORET COLOR | CAPITULUM FORM AND TYPE | BRANCHING PATTERN |
|---|---|---|---|
| EN GARDE | RED-PURPLE | FLAT DECORATIVE | SEMI-SPREADING |
| TEMPO | DARK LAVENDER | FLAT DECORATIVE | SEMI-SPREADING |

| CULTIVAR | DIAMETER ACROSS FACE OF CAPITULUM | PLANT HEIGHT | FLOWERING RESPONSE PERIOD | TEMPERATURE TOLERANCE |
|---|---|---|---|---|
| EN GARDE | 9 to 10 cm. | MEDIUM | EIGHT WEEKS | LOW - 13° C. MINIMUM HIGH - 24° C. NIGHT to 38° C. DAY |
| TEMPO | 11 to 13 cm. | TALL | EIGHT TO NINE WEEKS | LOW - 16° C. HIGH - SLOWS TO ELEVEN WEEKS |

COMPARISONS MADE OF PLANTS GROWN AS PINCHED DISBUDDED POT MUMS IN SALINAS, CALIFORNIA AND LEAMINGTON, ONTARIO, CANADA

I claim:

1. A new and distinct cultivar of *Chrysanthemum morifolium,* Ramat., plant named En Garde, as described and illustrated, and particularly characterized as to uniqueness by the combined characteristics of flat capitulum form; decorative capitulum type; red-purple ray floret color; diameter across face of capitulum ranging from 9 to 10 cm. at maturity; uniform eight week flowering response; medium plant height; semi-spreading branching pattern; and tolerance of both low winter 13° C. minimum and high summer 24° C. night to 38° C. temperatures for bud initiation and flower development.

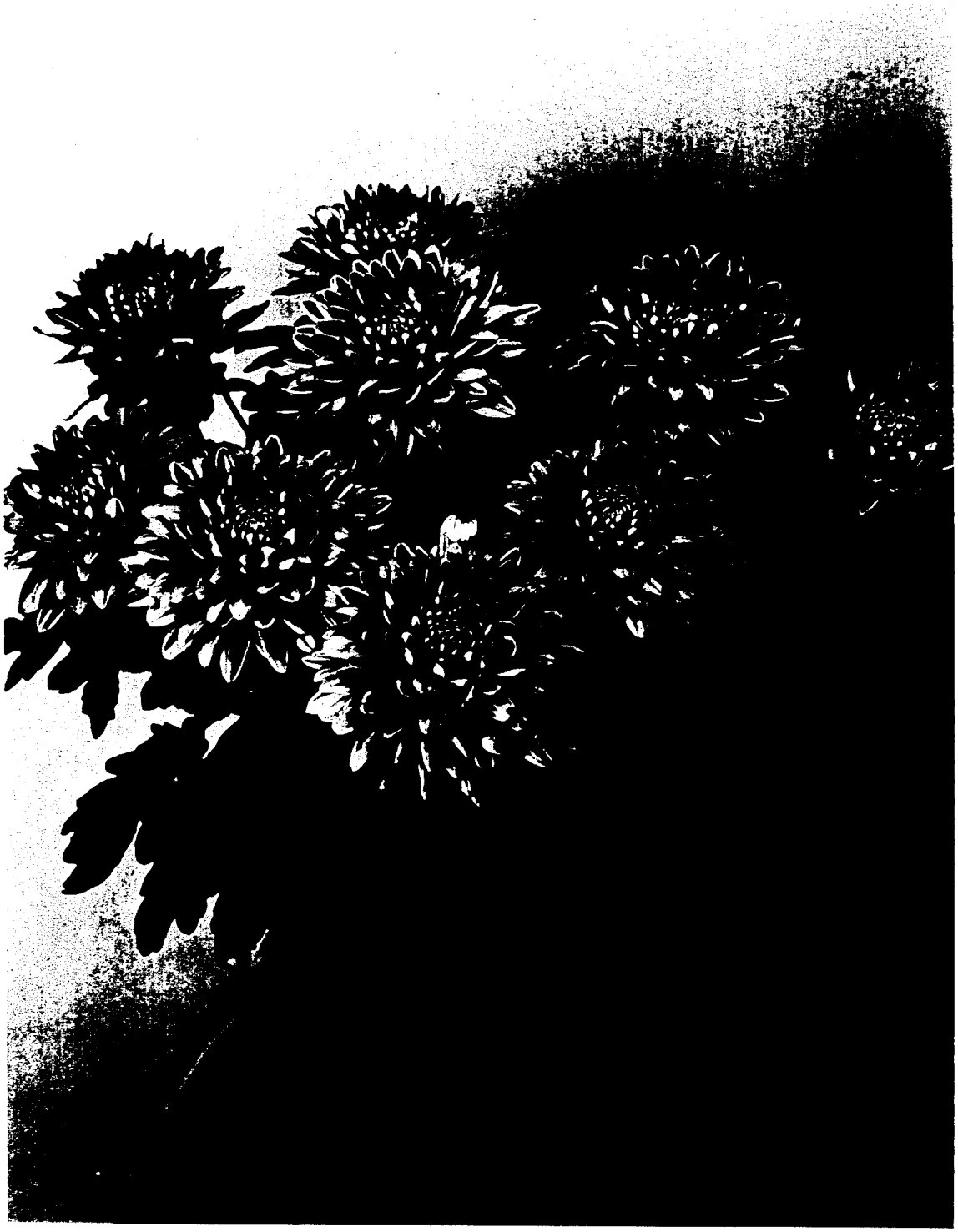

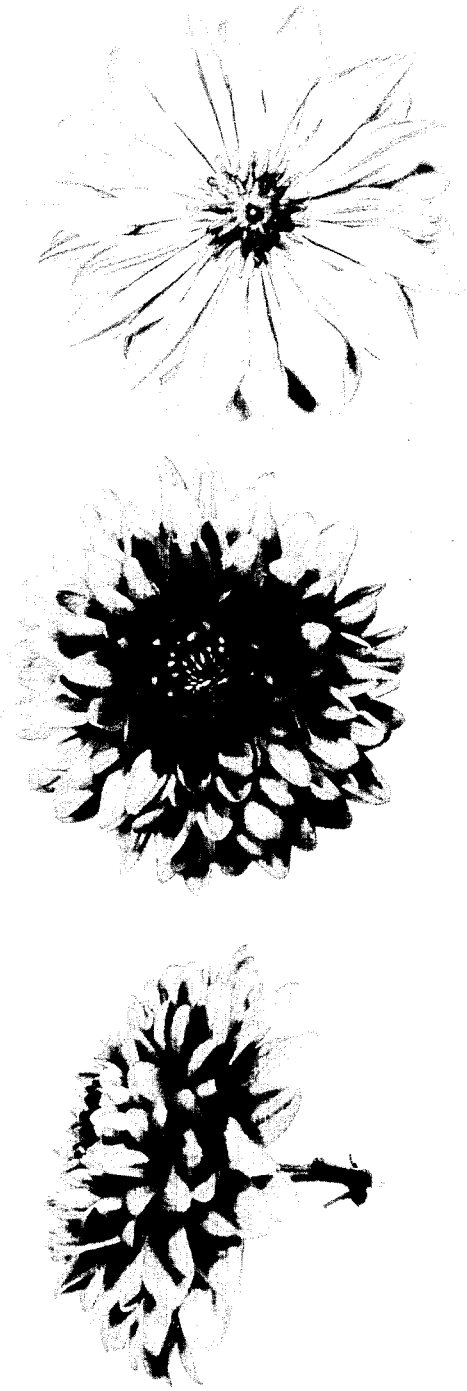

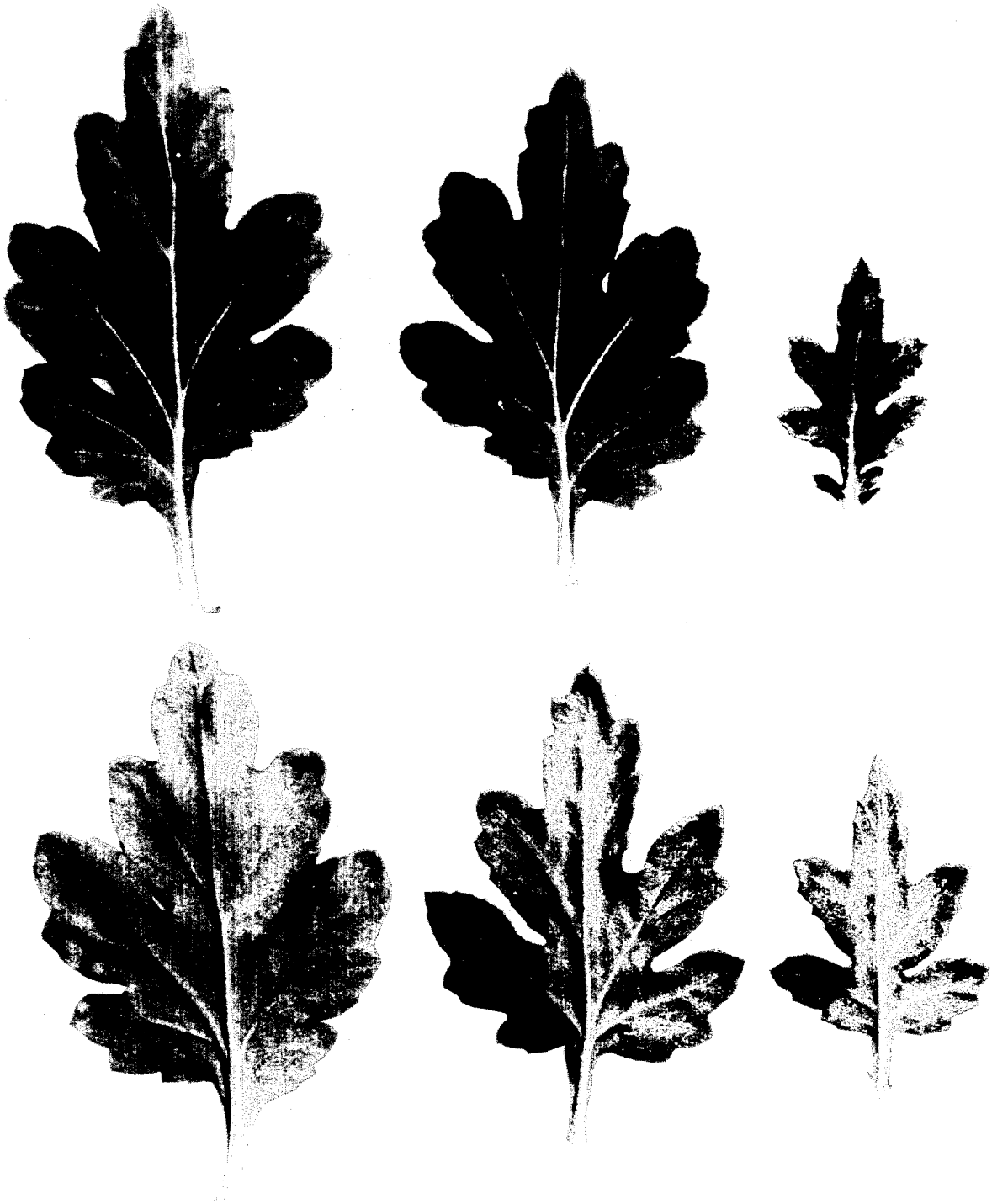

* * * * *